United States Patent
Agnew

(10) Patent No.: US 7,736,385 B2
(45) Date of Patent: Jun. 15, 2010

(54) EXCHANGEABLE DELIVERY SYSTEM WITH DISTAL PROTECTION

(75) Inventor: Charles W. Agnew, West Lafayette, IN (US)

(73) Assignee: Cook Incorporated, Bloomington, IN (US)

(*) Notice: Subject to any disclaimer, the term of this patent is extended or adjusted under 35 U.S.C. 154(b) by 646 days.

(21) Appl. No.: 11/388,906

(22) Filed: Mar. 24, 2006

(65) Prior Publication Data

US 2006/0229702 A1  Oct. 12, 2006

Related U.S. Application Data

(60) Provisional application No. 60/664,851, filed on Mar. 24, 2005.

(51) Int. Cl.
*A61F 2/06* (2006.01)

(52) U.S. Cl. .............. 623/1.12; 606/195; 606/200

(58) Field of Classification Search ............ 623/1.11, 623/1.12; 606/195, 200
See application file for complete search history.

(56) References Cited

U.S. PATENT DOCUMENTS

| 4,762,129 A | 8/1988 | Bonzel |
| 6,200,336 B1 | 3/2001 | Pavcnik et al. |
| 6,616,680 B1 | 9/2003 | Thielen |
| 7,182,779 B2 * | 2/2007 | Acosta et al. ............ 623/1.11 |
| 2003/0212431 A1 | 11/2003 | Brady et al. |
| 2004/0064067 A1 | 4/2004 | Ward |
| 2004/0073230 A1 | 4/2004 | Mulholland et al. |
| 2004/0167566 A1 | 8/2004 | Beulke et al. |
| 2004/0186558 A1 | 9/2004 | Pavcnik et al. |
| 2004/0260389 A1 | 12/2004 | Case et al. |
| 2006/0282157 A1 | 12/2006 | Hill et al. |

FOREIGN PATENT DOCUMENTS

EP  1179321 A2  2/2002

OTHER PUBLICATIONS 8 pages—Schneider (Eur.) AG v. Scimed Life Sys., 852 F. Supp. 813 (D. Minn. 1994).

* cited by examiner

*Primary Examiner*—Todd E Manahan
*Assistant Examiner*—Michael G Mendoza
(74) *Attorney, Agent, or Firm*—Buchanan Intellectual Property Office LLC

(57) ABSTRACT

Medical device delivery systems that include a distal protection feature are provided. A distal tip member that includes a distal protection device and a mounting region for a self-expandable, intraluminal medical device is slidably disposed within a passageway defined by a tubular member.

13 Claims, 9 Drawing Sheets

EXCHANGEABLE DELIVERY SYSTEM WITH DISTAL PROTECTION

CROSS REFERENCE TO RELATED APPLICATIONS

The present patent application claims priority to the provisional patent application identified by U.S. Ser. No. 60/664,851, filed on Mar. 24, 2005, the entire contents of which is hereby expressly incorporated herein by reference.

FIELD OF THE INVENTION

The invention relates to delivery systems for placement of self-expandable intraluminal medical devices within a body vessel.

BACKGROUND OF THE INVENTION

Minimally invasive medicine, the practice of gaining access to a body vessel, duct, or organ using a guiding member to facilitate the subsequent introduction of other medical devices, has been evolving since the Seldinger technique was first popularized during the 1950's and 1960's. In contemporary medicine, self-expandable intraluminal medical devices are frequently used in a variety of minimally invasive procedures. For example, self-expandable stents are used to provide support to various vessels and ducts in the circulatory and the gastrointestinal systems. Also, prosthetic valves and other intraluminal devices are gaining popularity as tools for supplementing and/or replacing natural valves in a variety of locations within the body, such as veins and the heart and its associated vessels.

When placing medical devices within a body vessel, it may be desirable to provide a protective device that can capture any solid mass, e.g., an embolus, that may travel through the circulation during the procedure. Permanent or semi-permanent filters can be implanted in a downstream location, such as within the inferior vena cava to provide the desired protection. Also, filters or other structures associated with a delivery system can be used to provide distal protection during and/or after a procedure.

As this field of health care continues to advance there is a need for improved methods and devices for use in these important techniques. There is a distinct need for delivery systems that offer distal protection features, especially delivery systems adapted for placement of self-expandable intraluminal medical devices.

SUMMARY OF EXEMPLARY EMBODIMENTS

Medical device delivery systems are provided. In one exemplary embodiment, a delivery system comprises an elongate tubular member with a circumferential wall and proximal and distal ends. The tubular member defines a passageway and includes a protrusion disposed on an inner surface at the distal end. A distal tip member is slidably disposed in the passageway and includes proximal and distal portions. A distal protection device is disposed on the distal portion and a self-expandable intraluminal medical device is disposed on a mounting region defined by the proximal portion.

Rapid exchange embodiments are provided and include an elongate tubular member having an exchange port defined by the circumferential wall.

The distal tip member can comprise a unitary member. Also, the proximal and distal portions of the distal tip member can comprise separable members joined at a junction.

Additional understanding of the invention can be obtained with review of the detailed description of exemplary embodiments, below, and the appended drawings illustrating exemplary embodiments.

DETAILED DESCRIPTION OF EXEMPLARY EMBODIMENTS

The following detailed description and the appended drawings describe and illustrate exemplary embodiments with the purpose of enabling one of ordinary skill in the relevant art to make and use the invention. The description and drawings are not intended to limit the scope of the invention, or its protection, in any manner.

Figure 1:
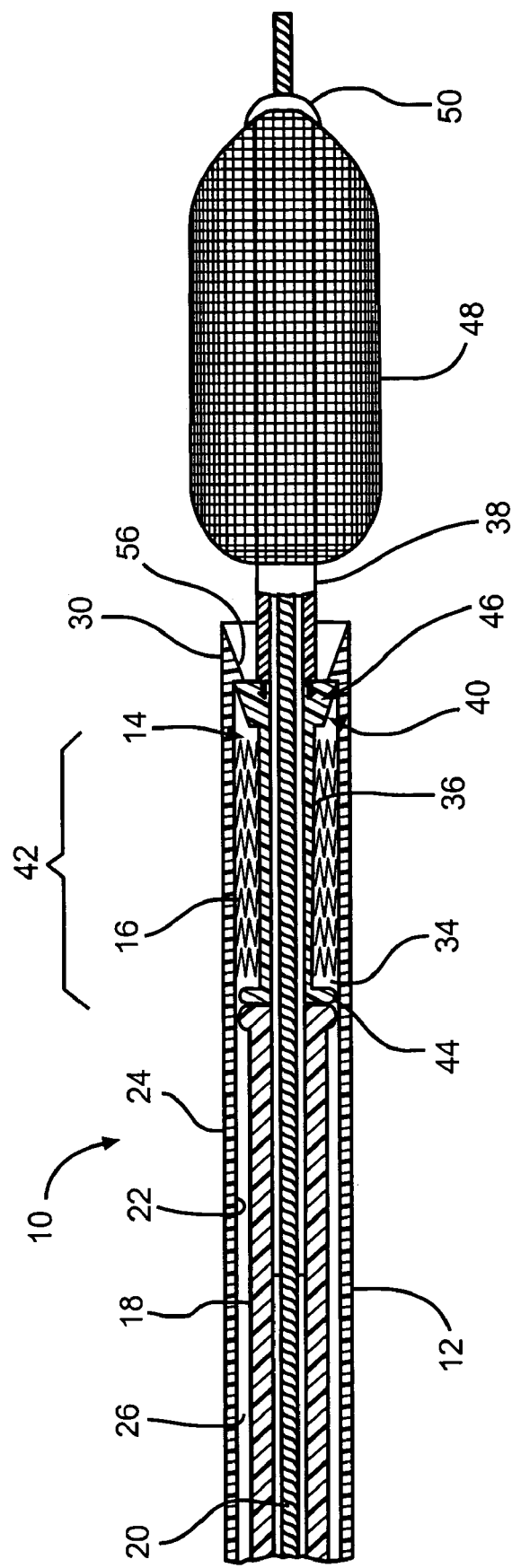
FIG. 1 is a sectional view of the distal end of a delivery system according to a first exemplary embodiment.
Figure 2:
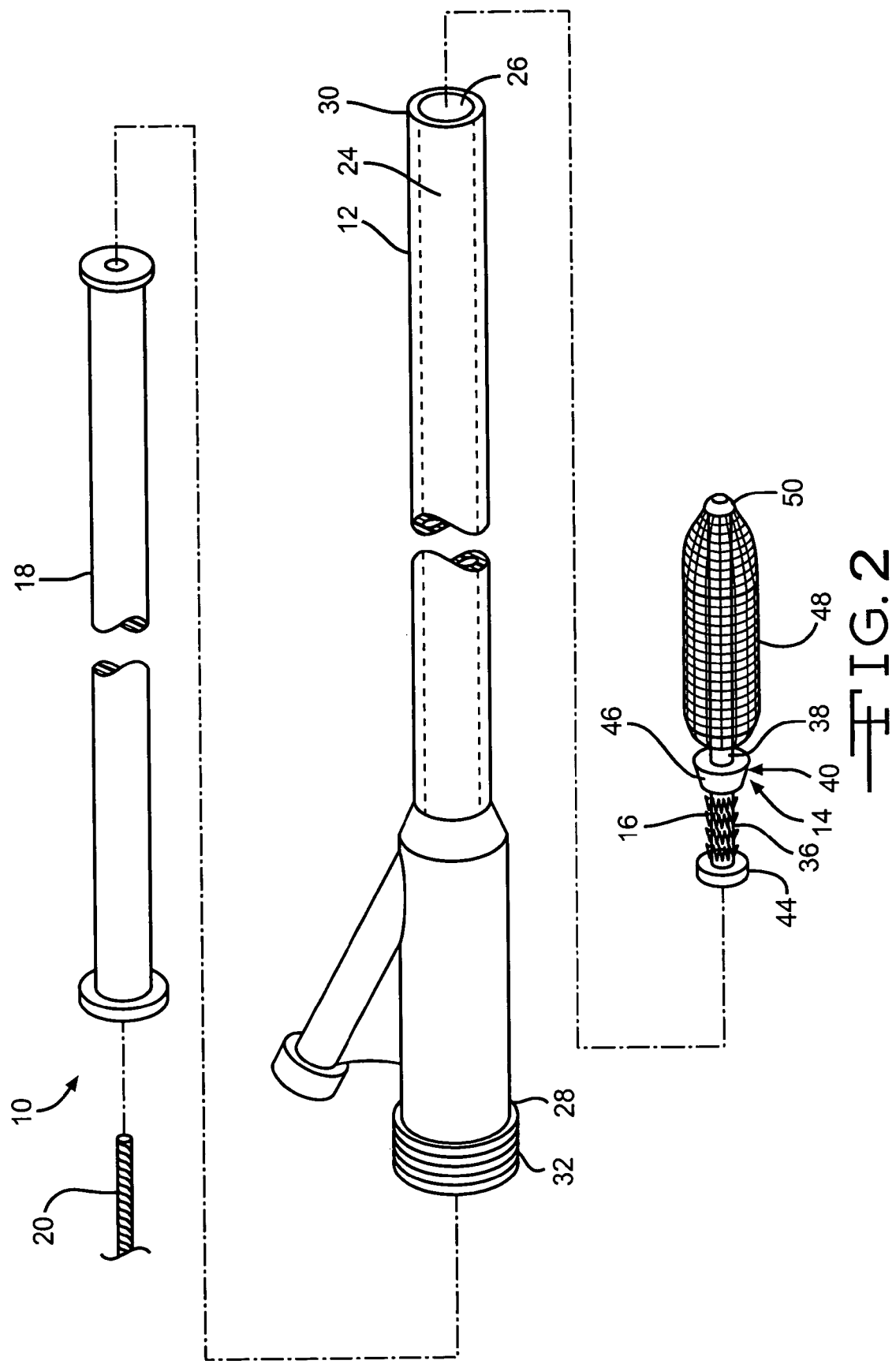
FIG. 2 is an exploded perspective view of the delivery system illustrated in FIG. 1.
Figure 3:
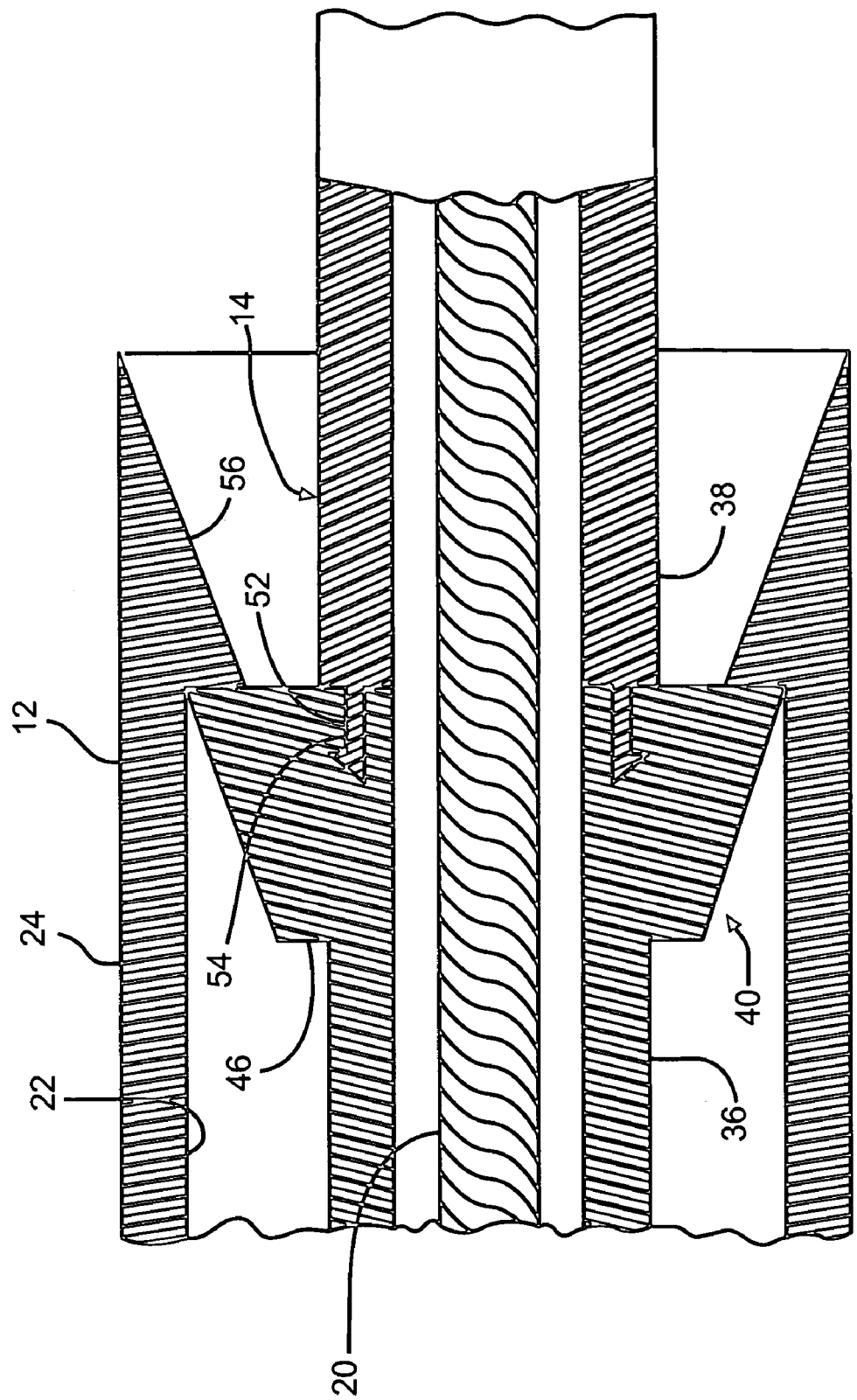
FIG. 3 is a magnified sectional view of the delivery system illustrated in FIG. 1.

FIGS. 1 through 3 illustrate a delivery system 10 according to a first exemplary embodiment of the invention. Delivery system 10 includes an elongate tubular member 12 and a distal tip assembly 14 slidably disposed within the elongate tubular member 12. A self-expandable intraluminal medical device 16 is disposed on a portion of the distal tip assembly 14 and, as best illustrated in FIG. 1, initially within the elongate tubular member 12 prior to deployment. A pusher 18 can be used to effect movement of the distal tip assembly 14 and ultimately deployment of the self-expandable intraluminal medical device 16. The entire delivery system 10 can be advanced over a wireguide 20 to navigate within a body vessel and ultimately to a point of treatment for deployment of the self-expandable intraluminal medical device 16.

The tubular member 12 can be any suitable tubular member, such as a sheath formed of plastic or other suitable material. Other examples of suitable tubular members include introducers, guiding catheters, and endoscopes. The tubular member 12 has inner 22 and outer 24 surfaces and defines a passageway 26 that extends between a proximal end 28 and a distal end 30. The passageway 26 provides a space within which other components of the delivery system 10 can be disposed. The proximal end 28 can include any desirable connectors and/or adapters, such as a threaded fitting 32, a Touhy-Borst adapter, and other suitable connectors and adapters. Also, a handle or handle system configured to allow sliding of the pusher 18 relative to the tubular member 12, or vice versa, could be attached to the proximal end 28 of the tubular member 12. These elements, however, are not required and the tubular member 12 can indeed comprise a simple tubular body.

The passageway 26 of the tubular member 12 includes a distal cavity 34 that receives at least a portion of the distal tip assembly 14. In the illustrated embodiment, the distal cavity 34 is a portion of and is continuous with the passageway 26. It is understood that, while the tubular member 12 is illustrated with a constant inner diameter along its length, varying inner diameters can be used, including varying inner diameters that, in effect, at least partially separate the distal cavity 34 from the remainder of the passageway 26.

The distal tip assembly 14 provides a structure for carrying the self-expandable intraluminal medical device 16. The distal tip assembly 16 comprises a separate member from the tubular member 12 and is at least partially slidably disposed within the distal cavity 34 of the tubular member 12. The distal tip assembly 14 includes proximal 36 and distal 38 portions that are joined at a junction 40. The junction 40 provides a temporary joint for joining the proximal 36 and distal 38 portions and is configured to allow separation of these portions. 36, 38, as is described more fully below. The proximal portion 36 provides a mounting region 42 on which the self-expandable intraluminal medical device 16 is disposed prior to deployment from the delivery system 10. A proximal flange 44 is disposed at the proximal end of the proximal portion 36 and a distal flange 46 is disposed at the distal end of the proximal portion 36. The proximal 44 and distal 46 flanges are spaced from one another to provide a mounting region 42 of sufficient length to accommodate the self-expandable intraluminal medical device 16. Accordingly, the space between the proximal 44 and distal 46 flanges, and thus the length of the mounting region 42, will vary depending on the nature of the self-expandable intraluminal medical device 16. A distal protection device 48 is disposed on the distal portion 38 of the distal tip assembly 14. A tip 50 is also disposed on the distal portion 38.

As best illustrated in FIG. 3, the junction 40 can comprise any suitable means for joining the proximal 36 and distal 38 portions of the distal tip assembly 14. In the illustrated embodiment, the junction 40 comprises barbs 52 disposed on a proximal end of the distal portion 38 and cavities 54 within the distal end of the proximal portion 36. The cavities 54 can be defined by the proximal portion 36 or the distal flange 46. No matter the structure, the means for joining the proximal 36 and distal 38 portions should provide a temporary junction 40 between the proximal 36 and the distal 38 portions. As will be described more fully below, the proximal portion 36 can be separated from the distal portion 38 during use of the delivery system 10.

The proximal 44 and distal 46 flanges both impede sliding of the distal tip assembly 14 within the distal cavity 34. Both flanges 44, 46 interact with a protrusion 56 disposed on the inner surface 22 of the tubular member 12. The distal flange 46, which encounters the protrusion 56 first during distally directed axial movement of the distal tip assembly 14, is configured to overcome the impedance provided by the protrusion 56 upon application of sufficient force. Once the distal flange 46 has overcome the protrusion 56, the distal tip assembly 14 can be advanced such that the mounting region 42 exits the distal cavity 34 of the tubular member 12. Ultimately, the proximal flange 44 encounters the protrusion 56 to stop distally directed axial movement of the distal tip assembly 14. The proximal flange 44 is configured such that it is substantially unable to move axially beyond the protrusion 56. That is, the protrusion 56 interacts with the proximal flange 44 to provide a mechanical stop to distally directed axial movement of the distal tip assembly 14 that cannot be overcome by application of additional force.

The distal protection device 48 can be any suitable means for capturing solid matter flowing through a body vessel, such as an embolus. Examples of suitable distal protection devices include self-expandable meshes, expandable filters including ordered, structural members, expandable filters including randomly arranged structural members, expandable balloons, and the like. Any structure capable of providing the desired ability to capture solid matter flowing through the bloodstream can be used. The specific structure used for the distal protection device in a particular embodiment will depend on several factors, including the nature and diameter of the body vessel in which the delivery system is being used. Expandable meshes formed of biocompatible materials, such as stainless steel are considered advantageous due to the ease of manufacture associated with such meshes and their flexibility, which facilitates their use in a variety of vessel types.

The tip 50 is the distal-most portion of the distal tip assembly 14. The tip 50 advantageously includes a rounded, conical or other atraumatic configuration as it is the leading surface of the delivery system 10 during navigation through body vessels.

The components of the distal tip assembly 14 can be formed of any suitable materials. The proximal 36 and distal 38 portions advantageously comprise metal or plastic tubular members. The distal flange 46 is advantageously formed of a pliable material, such as an elastomeric material, that enables the distal flange 46 to overcome the impedance provided by the protrusion 56. The proximal flange 44 is advantageously formed of a relatively rigid material 44 such as a plastic or metal material. In one exemplary embodiment, the proximal portion 36 comprises a unitary member formed of plastic. In this embodiment, the proximal flange 44 is continuous with the mounting region 42 of the proximal portion 36. Also in this embodiment, the distal flange 46 comprises a separate flexible member disposed on the proximal portion 36.

The self-expandable intraluminal medical device 16 can comprise any suitable type of self-expandable medical device, including self-expandable stents, valve devices that include a self-expandable support frame, such as prosthetic valves for implantation in a vein (prosthetic venous valves), or heart vessel and/or chamber, self-expandable filters, distal protection devices, vessel occluders, and other self-expandable devices. Suitable self-expandable medical devices for use with delivery systems according to the invention include those described in U.S. Pat. No. 6,200,336 to Pavcnik et al. for a MULTIPLE-SIDED INTRALUMINAL MEDICAL DEVICE; U.S. application for patent Ser. No. 10/642,372 of Pavcnik et al. for an IMPLANTABLE VASCULAR DEVICE, filed on Aug. 15, 2003; and U.S. application for Pat. Ser. No. 10/828,716 of Case, et al. for an ARTIFICAL VALVE PROSTHESIS WITH IMPROVED FLOW DYNAMICS, filed on Apr. 21, 2004; the entire disclosures of which are hereby incorporated into this disclosure for the purpose of describing suitable self-expandable intraluminal medical devices for use with delivery systems described herein.

The delivery system 10 can be operated in the following manner. First, a wireguide 20 is navigated through a body vessel beyond the points at which deployment of the distal protection device 48 and the self-expandable intraluminal medical device 16 is desired. Once the wireguide 20 is in an appropriate position, the delivery system 10 is navigated over the previously placed wireguide 20. Initially, the delivery system 10 is advanced to the point of treatment at which deployment of the distal protection device 48 is desired. Typically, this point of treatment will be distal to the point of treatment at which deployment of the self-expandable intraluminal medical device 16 is desired.

Once in proper position, deployment of the distal protection device 48 can be conducted either by retracting the tubular member 12 to expose the distal protection device 48 or by advancing the distal tip assembly 14 out of the distal cavity 34. A pusher 18 is advantageously used in each of these techniques. For example, during retraction of the tubular member 12, a pusher 18 can maintain the axial position of the distal tip assembly 14, ensuring deployment of the distal protection device 48. If axial advancement of the distal tip assembly is used, a pusher 18 can be used, in effect, to force the distal tip assembly 14 out of the distal cavity 34 to deploy the distal protection device 48.

Following deployment of the distal protection device 48, the delivery system 10 is retracted along the wire guide 20 to the point of treatment at which deployment of the self-expandable intraluminal medical device 16 is desired. Upon initiation of retraction, the protrusion 56 on the inner surface 22 of the tubular member engages the distal flange 46 of the proximal portion 36 of the distal tip assembly 14. This engagement is illustrated in FIGS. 1 and 3. Continued retraction of the delivery system 10 once engagement has occurred forces separation of the proximal 36 and distal 38 portion of the distal tip assembly 14. Separation occurs once the junction 40 between the proximal 36 and distal 38 portions is disturbed. Once the separation has occurred, the delivery system 10 can be further withdrawn within the body vessel leaving the distal protection device 48 at the first point of treatment while moving the delivery system 10 to the second point of treatment for deployment of the self-expandable intraluminal medical device 16. Once the second point of treatment is reached, deployment of the self-expandable intraluminal medical device 16 can be conducted. For this deployment, enough force must be applied to enable the distal flange 46 to overcome the impedance to axial movement of the proximal portion 36 provided by the protrusion 56. Accordingly, a pusher 18 is advantageously used to apply distally directed axial force onto the proximal portion 36 of the distal tip assembly 14. Once sufficient force is achieved, the distal flange 46 overcomes the impedance provided by the protrusion 56 and the mounting region 42 begins to exit the distal cavity 34. Continued distal movement of the proximal portion 36 forces the remainder of the mounting region 42 out of the distal cavity 34 until the proximal flange 44 engages the protrusion 56. At this point, the self-expandable intraluminal medical device 16 is fully deployed.

The delivery system 10 can now be retracted along the wire guide 20 and ultimately removed from the body vessel, leaving the self-expandable intraluminal medical device 16 at the second point of treatment. At this stage, the self-expandable intraluminal medical device 16 and the distal portion 38 of the distal tip assembly 14, including the distal protection device 48, are disposed about the wire guide 20. If the distal protection device 48 is to be left in place following the procedure, the wire guide 20 can be removed from the vessel. However, if removal of the distal protection device 48 is desired following the procedure, a retrieval device can be navigated along the wire guide 20 to the first point of treatment within the body vessel. The retrieval device will pass through the self-expandable intraluminal medical device 16 prior to engaging the distal portion 38 of the distal tip assembly 14 at the first point of treatment.

Figure 4:
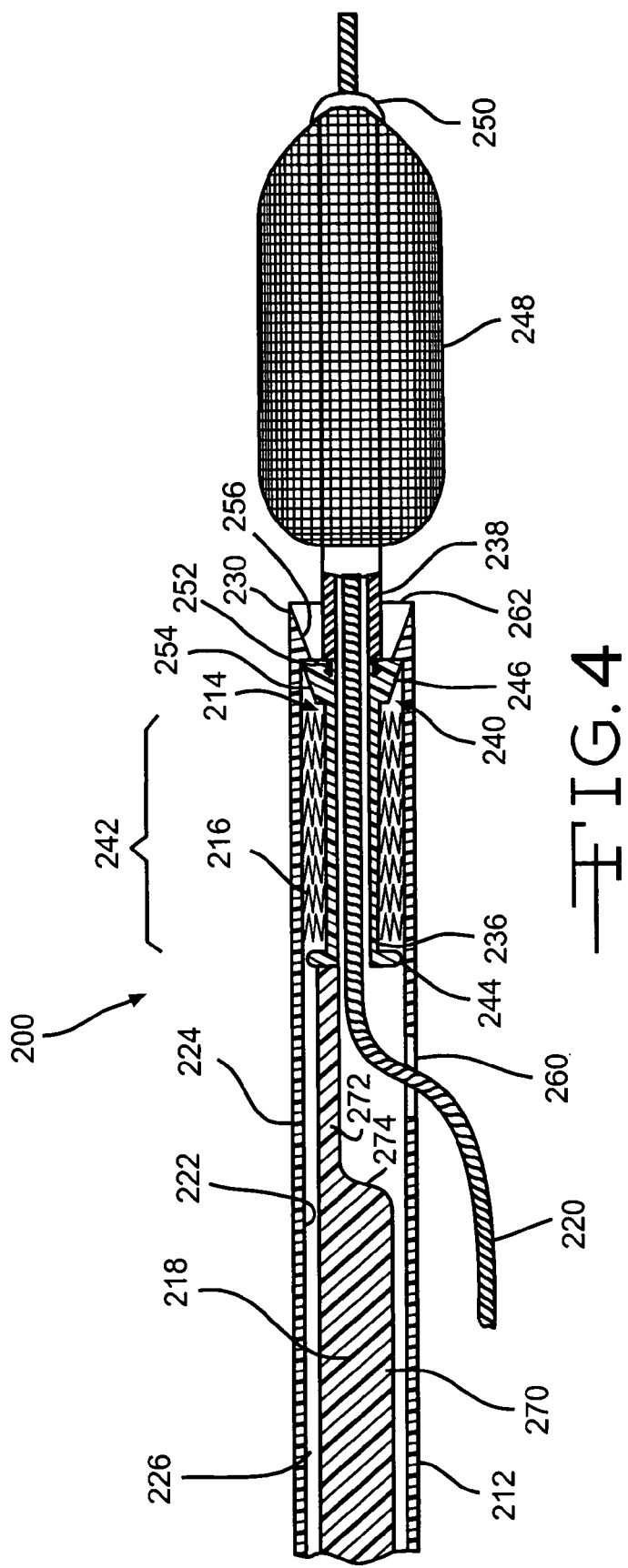
FIG. 4 is a sectional view of the distal end of a delivery system according to a second exemplary embodiment.

FIG. 4 illustrates a delivery system 200 according to a second exemplary embodiment of the invention. The delivery system 200 according to this embodiment is identical to the delivery system 100 illustrated in FIGS. 1 through 3, except as described below. Accordingly, the delivery system 200 includes a tubular member 212 and a distal tip assembly 214, a self-expandable intraluminal medical device 216 is disposed on the distal tip assembly 214. A pusher 218 is included and the delivery system 210 is placed over a wire guide 220. The tubular member 212 includes inner 222 and outer 224 surfaces and defines a passageway 226. The distal tip assembly 214 includes separable proximal 236 and distal 238 portions joined at a junction 240. The proximal portion 236 provides a mounting region 242 upon which the self-expandable intraluminal medical device 216 is disposed. A proximal flange 244 is disposed at the proximal end of the proximal portion 236 and a distal flange 246 is disposed on the distal end of the proximal portion 236. A distal protection device 248, such as a filter or other suitable device, is disposed on the distal portion 238.

The distal portion 238 of the distal tip assembly 214 includes a tip 250 and barbs 252 that are received by cavities 254 provided by the proximal portion 236. A protrusion 256 is disposed on the inner surface 222 of the tubular member 212 and is adapted to engage the flanges 244, 246.

The tubular member 212 of this embodiment is adapted for rapid exchange applications. Accordingly, the tubular member 212 defines an exchange port 260 in its side wall. The exchange port 260 comprises an opening that provides access from the external environment into the passageway 226 of the tubular member 212. The portion of the passageway 226 extending between the exchange port 260 and the opening 262 at the distal end 230 of the tubular member 212 provides a wire guide lumen that spans only a portion of the length of the tubular member 212. In use, a wire guide 220 passes through the opening 262 at the distal end 230 into the passageway 226 and exits the tubular member 212 through the exchange port 260. This configuration facilitates use of the delivery system 200 in rapid exchange techniques.

An alternative pusher 218 is also illustrated with this embodiment. The pusher 218 defines first 270 and second 272 axial portions that have different outer diameters. The second axial portion 272 has a relatively small outer diameter and the first axial portion 270 has a relatively larger outer diameter. A transition region 274 is disposed between first 270 and second 272 axial portions and transitions between the larger and smaller outer diameters. The second axial portion 272 is able to engage the proximal portion 236 of the distal tip assembly 214 despite the presence of the wire guide 220. The pusher 218 facilitates deployment of the distal protection device 248 and the self-expandable intraluminal medical device 216 in the rapid exchange arrangement of the wire guide 220 and tubular member 212.

Figure 5:
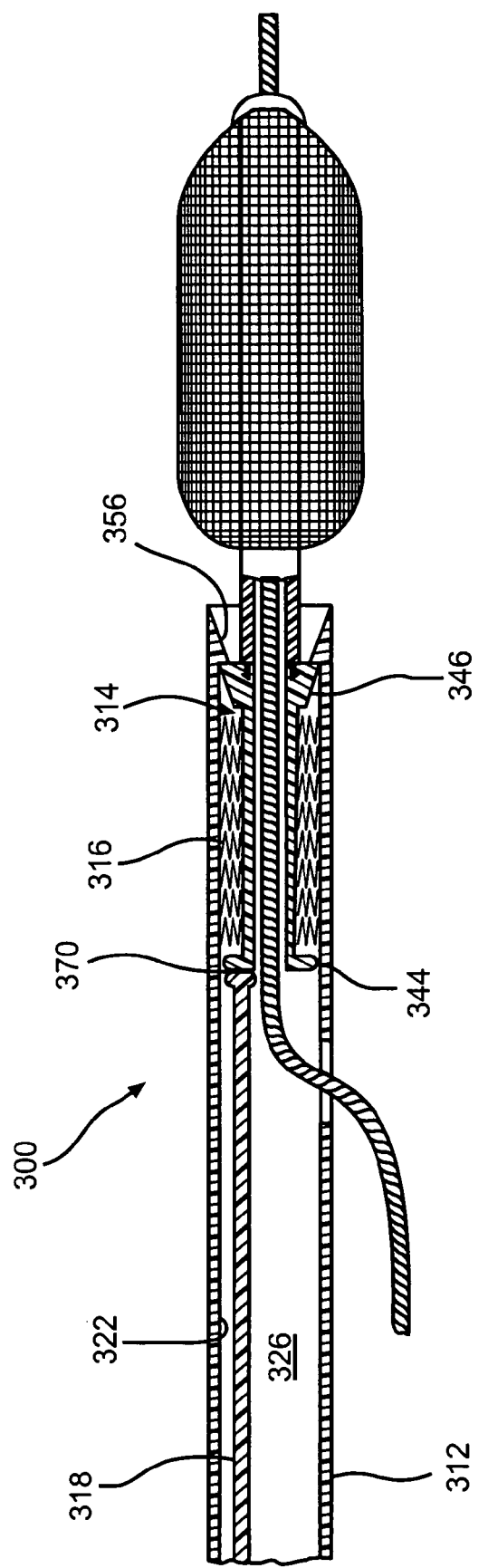
FIG. 5 is a sectional view of the distal end of a delivery system according to a third exemplary embodiment.

FIG. 5 illustrates a delivery system 300 according to a third exemplary embodiment of the invention. The delivery system 300 according to this embodiment is identical to the delivery system 200 illustrated in FIGS. 4, except as described below. Accordingly, the delivery system 300 includes a tubular member 312 and a distal tip assembly 314 slidably disposed within a passageway 326 defined by the tubular member 312. The distal tip assembly 314 includes proximal 344 and distal 346 flanges that engage a protrusion 356 disposed on the inner surface 322 of the tubular member 312. A self-expandable intraluminal medical device 316 is disposed on the distal tip assembly 314.

The pusher 318 in this embodiment comprises an elongate rod-like member with a distal pushing surface 370. The pusher 318 is advantageously formed of a relatively stiff material, such as a wire rod or hardened plastic. Also, hardened plastic including a wire core could be used.

Figure 6:
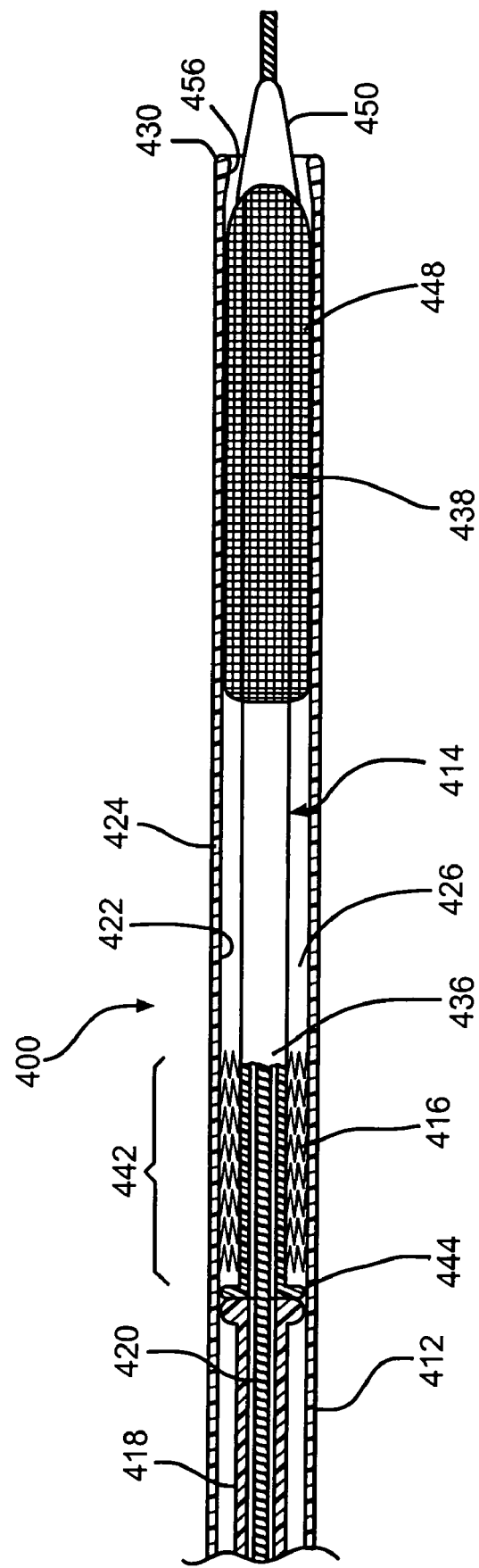
FIG. 6 is a sectional view of the distal end of a delivery system according to a fourth exemplary embodiment.
Figure 7:
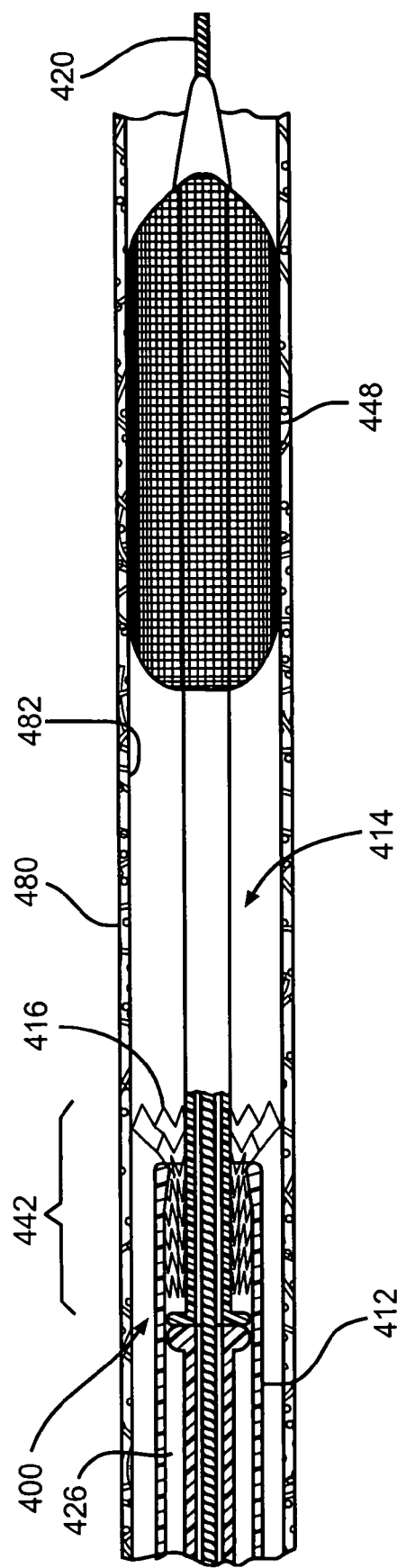
FIG. 7 is a sectional view of a body vessel containing the delivery system illustrated in FIG. 6. The delivery system is shown in a stage of a deployment procedure in which the distal protection device is fully deployed and the expandable intraluminal medical device is partially deployed.
Figure 8:
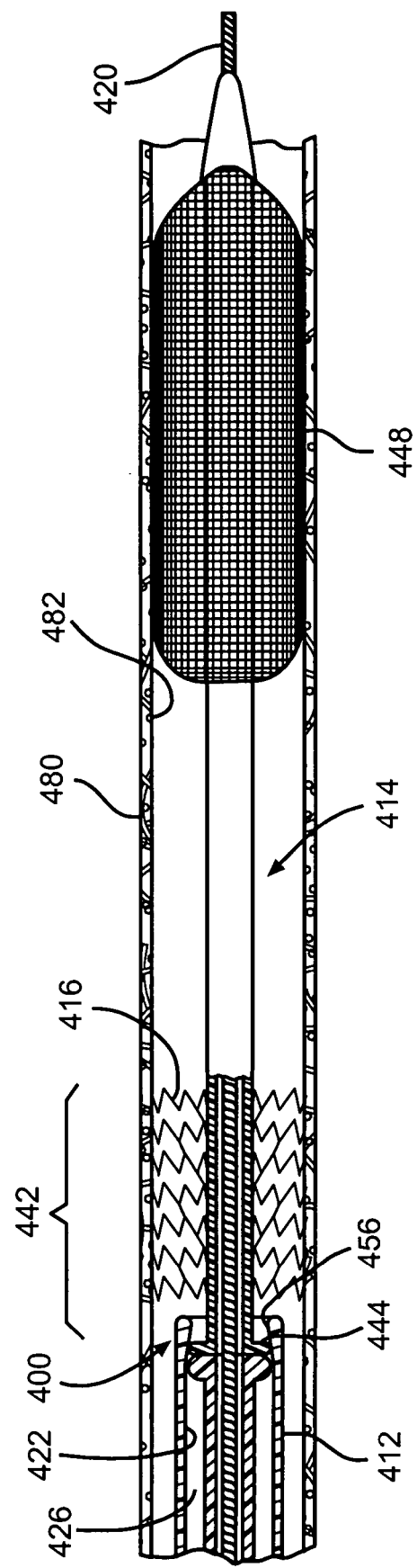
FIG. 8 is a sectional view of a body vessel containing the delivery system illustrated in FIG. 6. The delivery system is shown in a stage of a deployment procedure in which both the distal protection device and the expandable intraluminal medical device are fully deployed.

FIGS. 6 through 8 illustrate a delivery system 400 according to a fourth exemplary embodiment of the invention. The delivery system 400 includes a tubular member 412 and a distal tip assembly 414. A self-expanding intraluminal medical device 416 is disposed on the distal tip member 414. A pusher 418 is disposed within the tubular member 412 and provides a pushing surface for advancing the distal tip assembly 414 out of the tubular member 412. The delivery system 400 can be navigated within a body vessel over a previously placed wire guide 420. The tubular member 412 has inner 422 and outer 424 surfaces and defines a passageway 426 that extends between proximal and distal 430 ends.

The distal tip assembly 414 includes proximal 436 and distal 438 portions. In contrast to the previously described embodiments, the proximal 436 and distal 438 portions in this embodiment are continuous with one another and are not separable from each other. The proximal portion 436 provides a mounting region 442 upon which the self-expanding intraluminal medical device 416 is disposed. The distal tip assembly 414 includes a proximal flange 444 at its proximal end. A distal protection device 448 is disposed at the distal end of the distal tip assembly 414. A conical tip 450 including a tapered surface is disposed distal to the distal protection device 448.

A protrusion 456 is disposed on the inner surface 422 of the tubular member 412 and is configured to engage the proximal flange 444 of the distal tip assembly 414. The protrusion 456 is configured such that the distal tip assembly 414 can be advanced out of the passageway 426 of the tubular member 412 until the proximal flange 444 engages the protrusion 456. Engagement of the proximal flange 444 by the protrusion 456 provides sufficient impedance to further axial movement of the distal tip assembly 414 such that the distal tip assembly 414 cannot completely exit the passageway 426 of the tubular member 412.

FIGS. 7 and 8 illustrate operation of the delivery system 400 according to this embodiment. In both figures, the delivery system 400 is shown disposed over a wire guide 420 and within a body vessel 480. In FIG. 7, the distal tip assembly 414 has been forced out of the passageway 426 of the tubular member 412 such that the distal protection device 448 is fully deployed and engaging the inner wall 482 of the body vessel 480. Also, the distal tip assembly 414 has been advanced to a point at which a portion of the mounting region 442 as exited the passageway 426 of the tubular member 412. As a result, the self-expanding intraluminal medical device 416 is partially deployed, i.e., partially engaging the inner wall 482 of the body vessel 480.

In FIG. 8, the distal tip assembly 414 has been advanced to a point at which the proximal flange 444 has engaged the protrusion 456 on the inner surface 422 of the tubular member 412. As a result, the mounting region 442 of the distal tip assembly 414 has substantially exited the passageway 426 of the tubular member 412 and the self-expandable intraluminal medical device 416 is fully deployed. The protrusion 456 provides sufficient impedance upon engagement of the proximal flange 444 so that further distal movement of the distal tip assembly 414 is substantially prevented. This ensures that the distal tip assembly 414 will not completely exit the tubular member 412.

The distal tip assembly 414 has a length sufficient to place the distal protection device 448 and the self-expandable intraluminal medical device 416 at a desired distance from each other upon deployment. Any suitable distance can be used in the specific distance chosen for any particular delivery system according to the invention will depend on several considerations including a vessel in which the self-expandable intraluminal medical device 416 is being deployed.

The delivery system 400, according to this embodiment, is designed to provide distal protection during the deployment of the self-expandable intraluminal medical device. Because the distal tip assembly 414 does not completely exit the tubular member 412 the distal protection provided by the delivery system 400 according to this embodiment is temporary in nature. The distal protection device 448 is retrieved from the body vessel following deployment of the self-expandable intraluminal medical device 416. The retrieval of the distal protection device 448 can be accomplished by advancing the tubular member 412 through the self-expandable intraluminal medical device 416 following its deployment. Because the distal protection device 448 engages the inner wall 482 of the body vessel 480, the distal tip assembly 414 will remain substantially stationary while the tubular member 414 is advanced through the deployed self-expandable intraluminal medical device 416 and toward the distal protection device 448. Ultimately, the distal end of the tubular member 412 will engage the distal protection device 448. At this point, the distal protection device 448 can be resheathed by the tubular member 412 by applying sufficient additional distally directed axial force, effectively disrupting the engagement of the inner wall 482 of the body vessel 480 by the distal protection device 448. Once the distal protection device 448 has been completely resheathed within the tubular member 412 the entire delivery system 400 can be retracted along the wire guide 420 and ultimately removed from the body vessel 480 to leave the self-expandable intraluminal medical device 416 deployed at the point of treatment.

Figure 9:
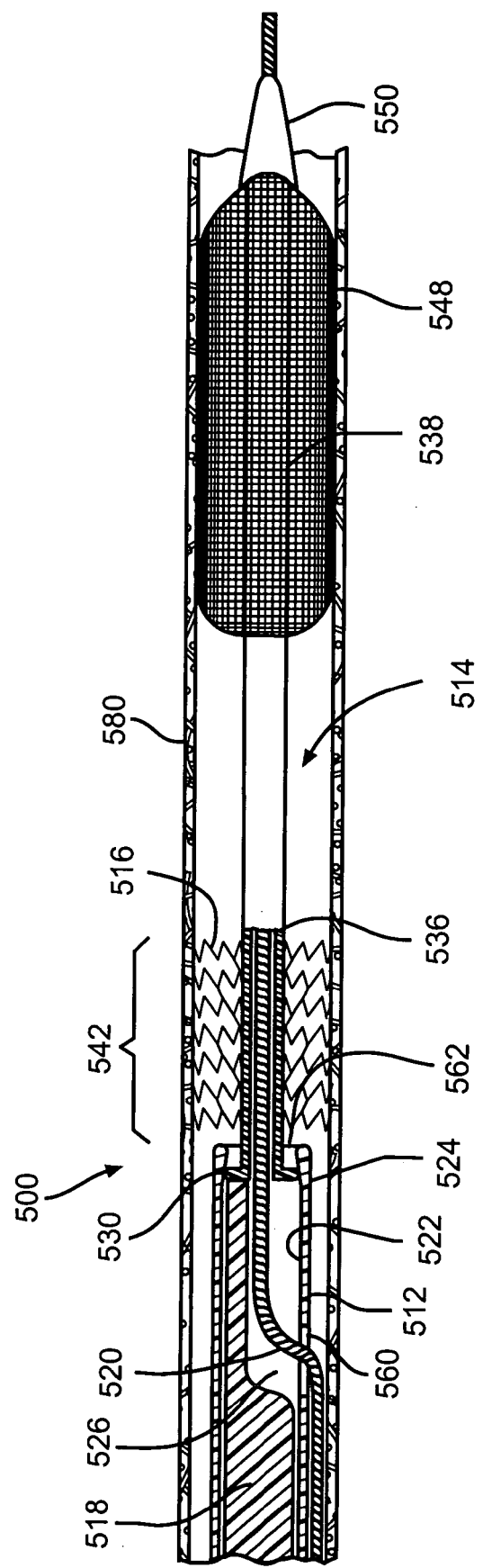
FIG. 9 is a sectional view of a body vessel containing a delivery system according to a fifth exemplary embodiment. The delivery system is shown in a stage of a deployment procedure in which both the distal protection device and the expandable intraluminal medical device are fully deployed.

FIG. 9 illustrates a delivery system 500 according to a fifth exemplary embodiment of the invention. The delivery system 500 according to this embodiment is similar to the delivery system 400 illustrated in FIGS. 6 through 8, except as below. Accordingly, the delivery system 500 includes a tubular member 512 and a distal tip assembly 514. A self-expandable intraluminal medical device 516 is disposed on the distal tip assembly 514. A pusher 518 is disposed within the tubular member 512 and provides a pushing surface for advancing the distal tip assembly 514 out of the tubular member 512. The delivery system 500 can be navigated through a body vessel 580 into a point of treatment over a previously placed guide wire 520.

The tubular member 512 includes inner 522 and outer 524 surfaces and defines a passageway 526 that extends between proximal and distal 530 ends.

The distal tip assembly 514 includes proximal 536 and distal 538 portions. The proximal portion 536 provides a mounting region 542 upon which the self-expandable intraluminal medical device 516 is disposed. The distal portion 538 includes a distal protection device 548, such as a self-expandable filter. A distal tip 550 is also disposed on the distal portion 538 of the distal tip assembly 514.

The delivery system 500 according to this embodiment is adapted for rapid exchange applications. Accordingly, the tubular member 512 defines an exchange port 560 in its side wall. A wireguide 520 can pass through a wireguide lumen that extends between an opening 562 disposed at the distal end 530 of the tubular member 512 and the exchange port 560.

The foregoing disclosure includes the best mode of the inventor for practicing the invention. It is apparent, however, that those skilled in the relevant art will recognize variations of the invention that are not described herein. While the invention is defined by the appended claims, the invention is not limited to the literal meaning of the claims, but also includes these variations.

What is claimed is:

1. A medical device delivery system comprising:
an elongate tubular member comprising a circumferential wall and having first proximal and distal ends, the elongate tubular member defining a passageway extending between the first proximal and distal ends and having a protrusion disposed on an inner surface at the distal end;
a distal tip member slidably disposed within the first passageway and having proximal and distal portions, the proximal portion defining a mounting region;
a distal protection device disposed on the distal portion of the distal tip member; and
a self-expandable intraluminal medical device disposed on the mounting region of the distal tip member;
wherein the proximal portion includes second proximal and distal ends and the distal tip member includes a proximal flange disposed on the second proximal end and adapted to engage the protrusion;
further comprising a distal flange disposed on the second distal end, the distal flange adapted to temporarily engage the protrusion;
wherein the proximal and distal portions comprise separate members;
wherein the distal tip member further comprises a separable junction joining the proximal and distal portions; and
wherein the separable junction comprises at least one barb disposed on the distal portion and at least one cavity adapted to receive the at least one barb.

2. The medical device delivery system according to claim 1, wherein the distal flange comprises a pliable material.

3. The medical device delivery system according to claim 1, wherein the proximal flange comprises a rigid material.

4. The medical device delivery system according to claim 1, wherein the at least one cavity is formed in the second distal end.

5. The medical device delivery system according to claim 1, wherein the at least one cavity is formed in the distal flange.

6. The medical device delivery system according to claim 1, wherein the circumferential wall defines an exchange port extending through the circumferential wall and providing access to the passageway.

7. The medical device delivery system according to claim 1, wherein the self-expandable intraluminal medical device comprises a stent.

8. The medical device delivery system according to claim 1, wherein the self-expandable intraluminal medical device comprises a prosthetic valve.

9. The medical device delivery system according to claim 1, wherein the distal protection device comprises a self-expandable mesh.

10. The medical device delivery system according to claim 9, wherein the self-expandable mesh is formed of stainless steel.

11. The medical device delivery system according to claim 1, wherein the self-expandable intraluminal medical device comprises a self-expandable filter.

12. The medical device delivery system according to claim 1, wherein the self-expandable intraluminal medical device comprises a vessel occluder.

13. The medical device delivery system according to claim 8, wherein the prosthetic valve comprises a prosthetic venous valve.

* * * * *